United States Patent

Israel et al.

[11] Patent Number: 5,246,022
[45] Date of Patent: Sep. 21, 1993

[54] APPARATUS FOR HOLDING DENTAL FLOSS CONTAINERS AND SPOOLS

[76] Inventors: Gina Israel, 5615 N. Richmond, 2nd Flr., Chicago, Ill. 60659; Bonnie S. LaRussa, 17014 E. Deerskin Dr., Fountain Hills, Ariz. 85268

[21] Appl. No.: 701,204

[22] Filed: May 16, 1991

Related U.S. Application Data

[63] Continuation-in-part of Ser. No. 225,775, Jul. 29, 1988.

[51] Int. Cl.⁵ .............................................. A61C 15/00
[52] U.S. Cl. .................................... 132/324; 132/325; 206/63.5; 206/409
[58] Field of Search ............... 132/321, 323, 324, 325, 132/326, 327, 328, 329; 206/63.5, 409; 220/410; 221/31, 64, 66, 197, 198, 287, 307, 309, 310, 312 C; 211/65

[56] References Cited

U.S. PATENT DOCUMENTS

| | | | |
|---|---|---|---|
| 2,893,405 | 7/1959 | Castelli | 132/321 |
| 2,929,541 | 3/1960 | Castelli et al. | 132/321 |
| 3,789,859 | 2/1974 | Chambers | 132/326 |
| 3,830,247 | 8/1974 | Kephalakos | 132/322 |
| 4,140,222 | 2/1979 | Francevilla | 211/65 |
| 4,178,947 | 12/1979 | McCourry et al. | 132/324 |
| 4,286,611 | 9/1981 | Talbot | 132/321 |
| 4,327,755 | 5/1982 | Endelson | 132/324 |
| 4,753,254 | 6/1988 | McCullough et al. | 132/324 |
| 4,844,104 | 7/1989 | Martin | 132/321 |
| 4,881,560 | 11/1989 | Blaule et al. | 132/324 |
| 4,934,523 | 6/1990 | Strom | 132/326 |
| 5,067,503 | 11/1991 | Stile | 132/323 |
| 5,076,423 | 12/1991 | Russaek | 132/325 |

*Primary Examiner*—Gene Mancene
*Assistant Examiner*—Frank A. LaViola
*Attorney, Agent, or Firm*—Patula & Associates

[57] ABSTRACT

A dental floss container holder and floss dispenser having a housing with a front and back portion. A contoured resilient holding device made of closed or open cell foam or neoprene for retaining various shaped dental floss containers and spools. A retaining device may be affixed to the interior of the housing for releasably holding the floss containers within the housing. A guide directs floss from the retained container to the exterior of the housing. A cutter is positioned on the exterior of the housing. The housing may be wall mountable.

14 Claims, 9 Drawing Sheets

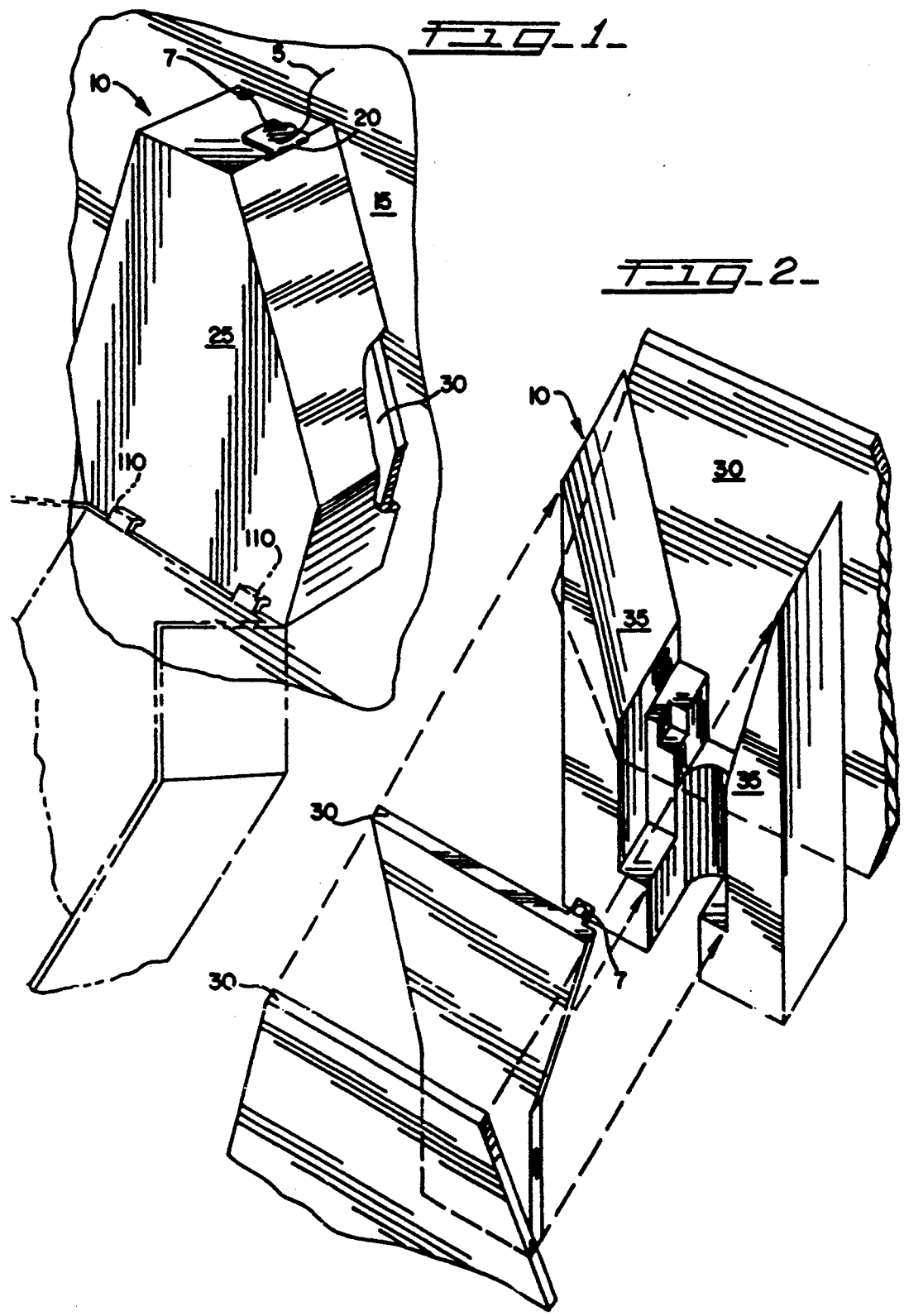

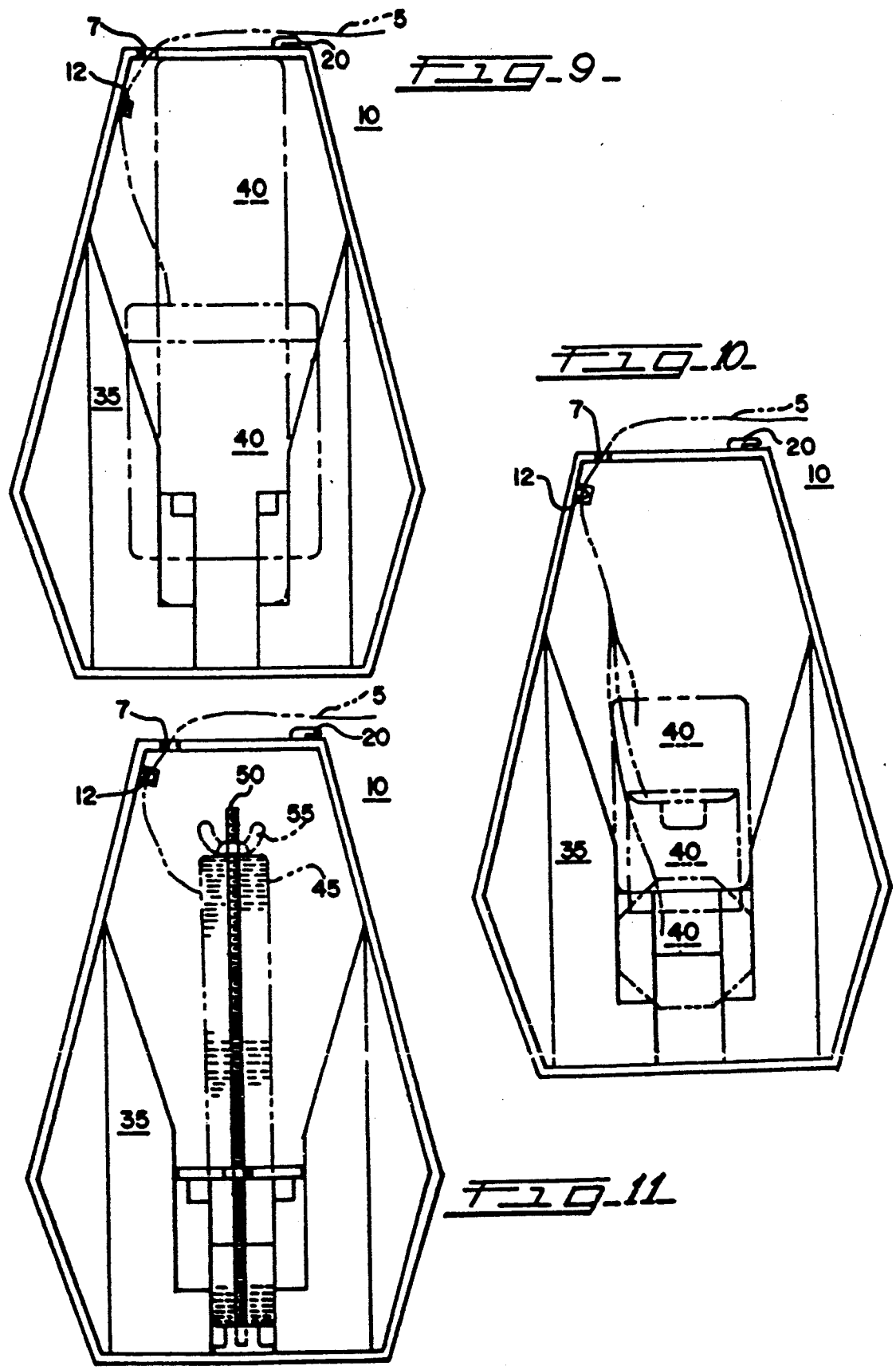

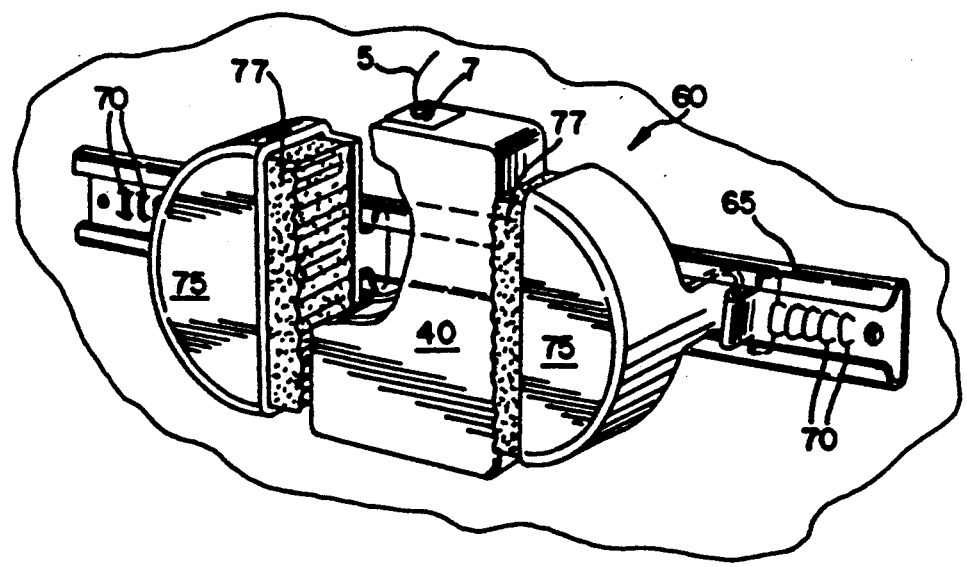
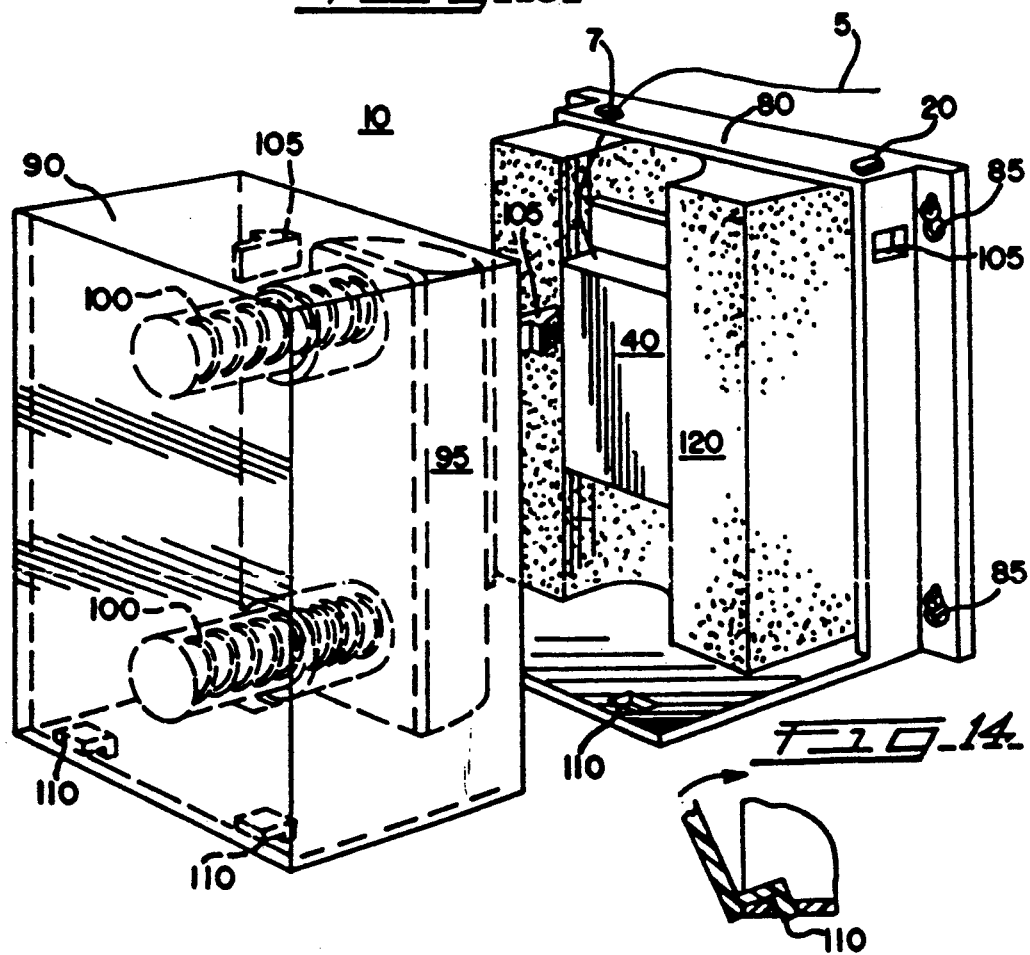

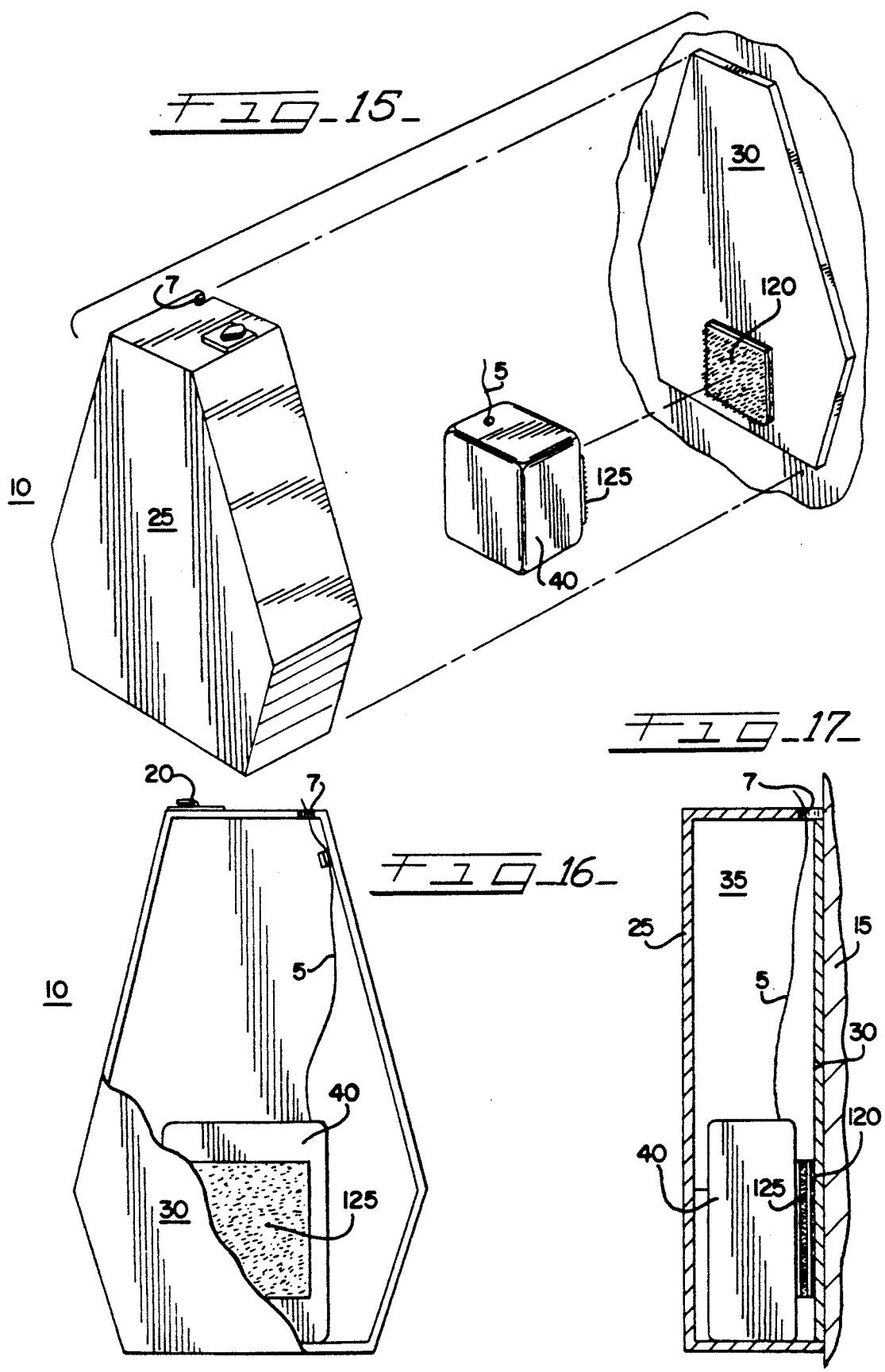

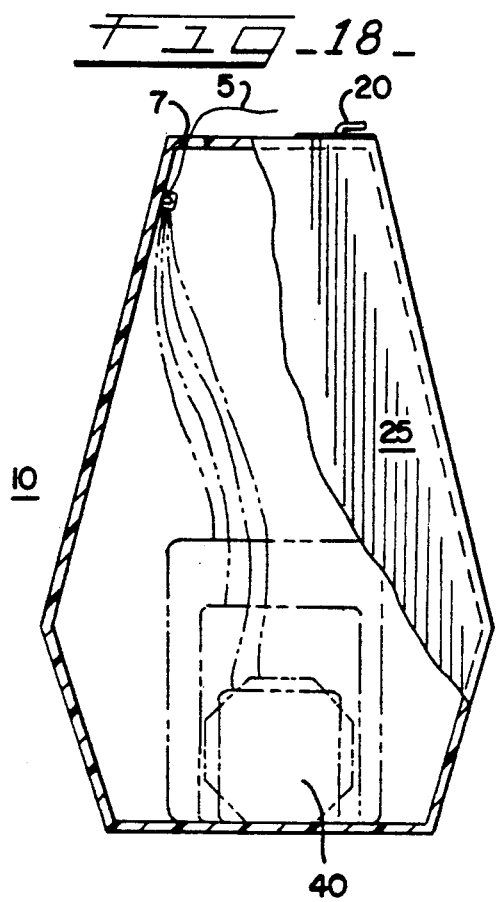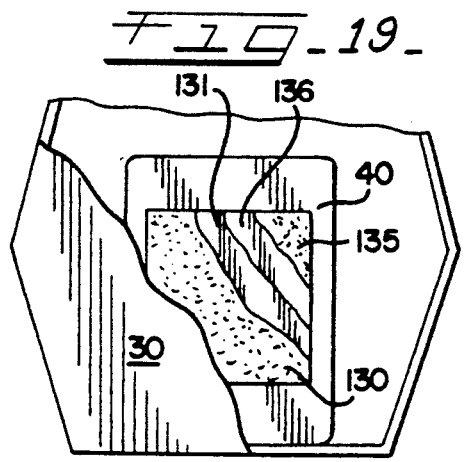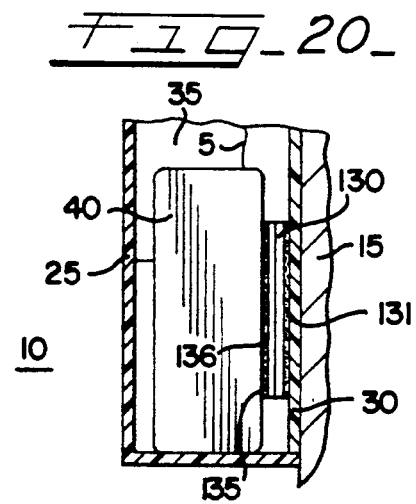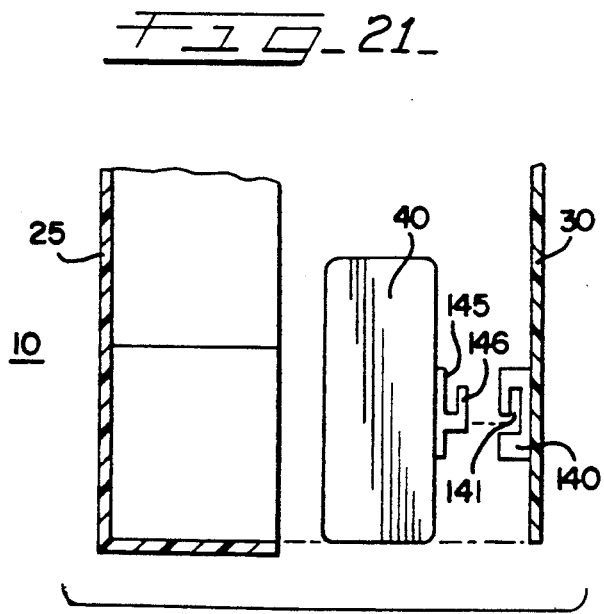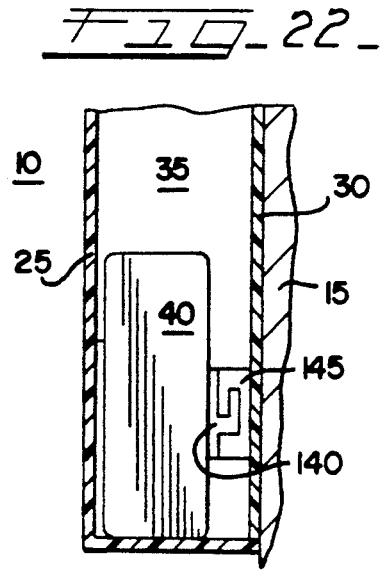

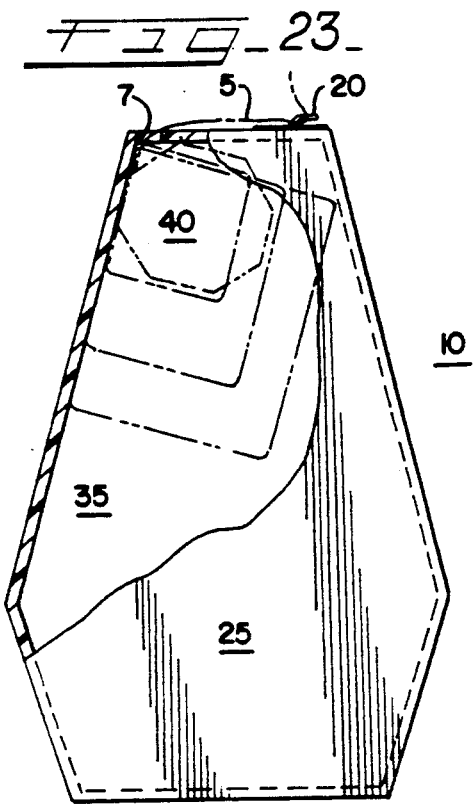
FIG_23_
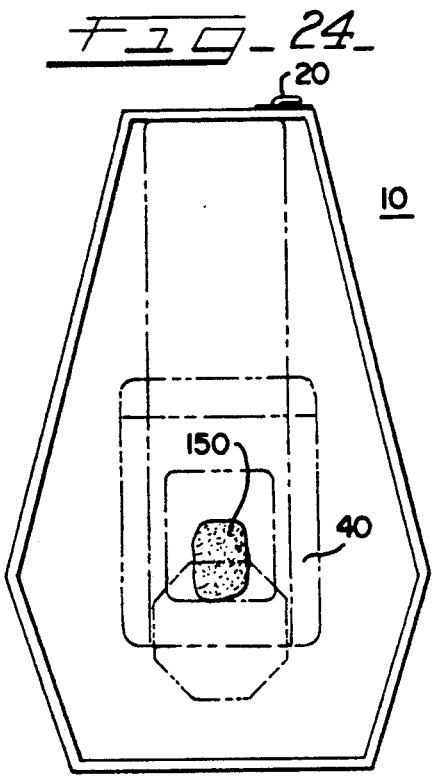
FIG_24_
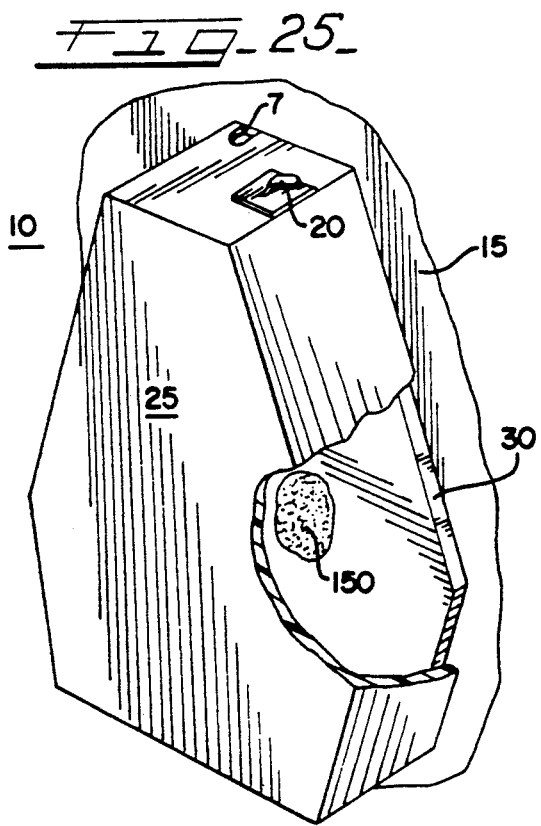
FIG_25_
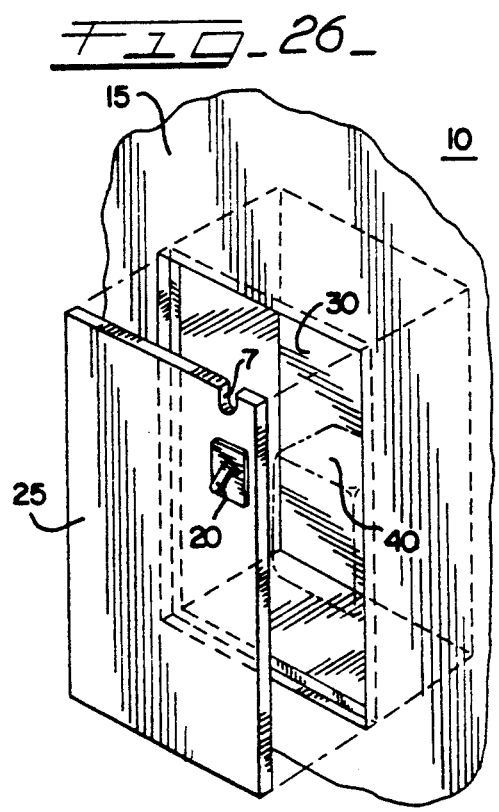
FIG_26_

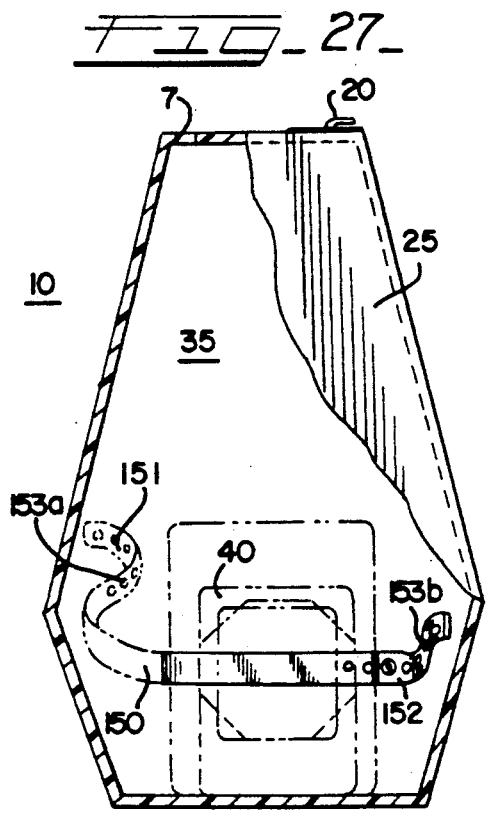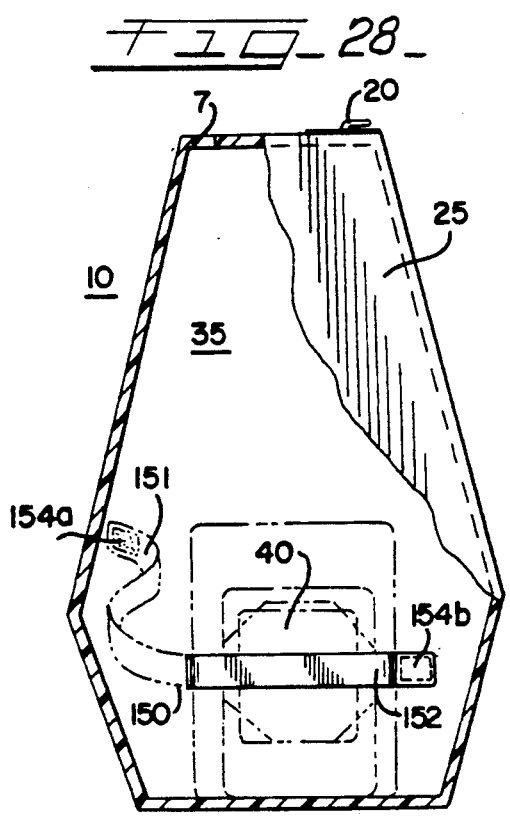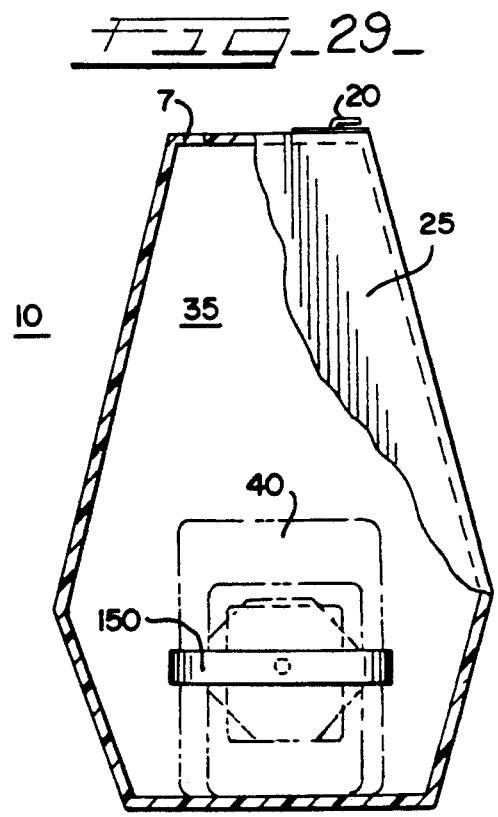

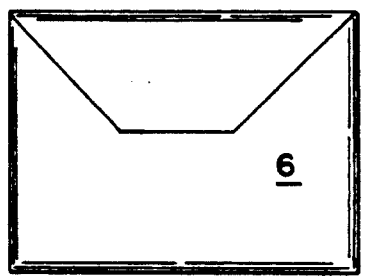
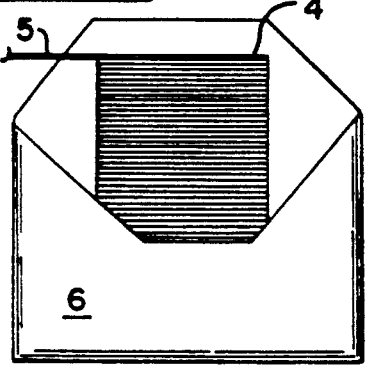
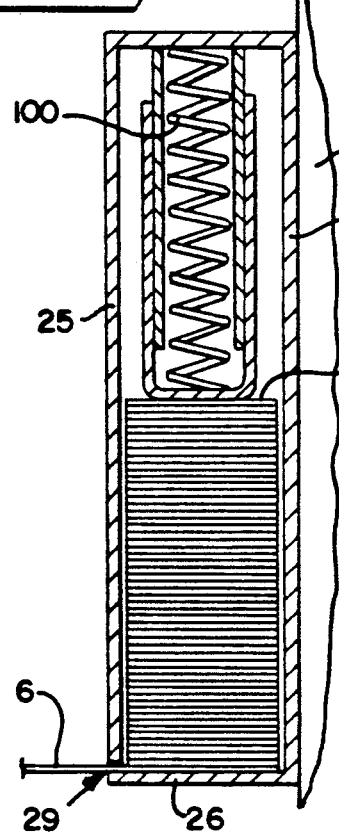
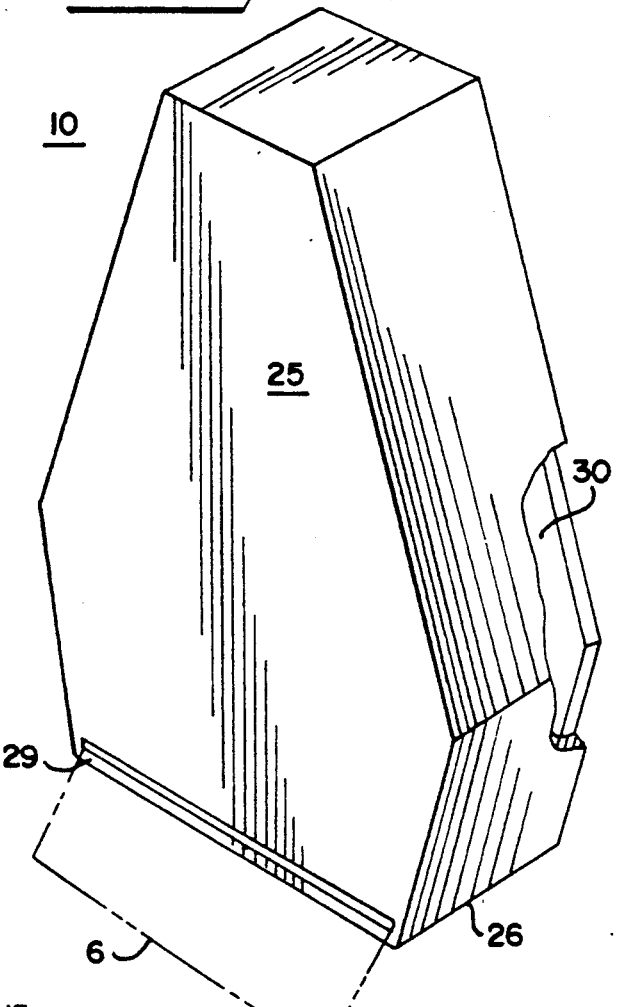
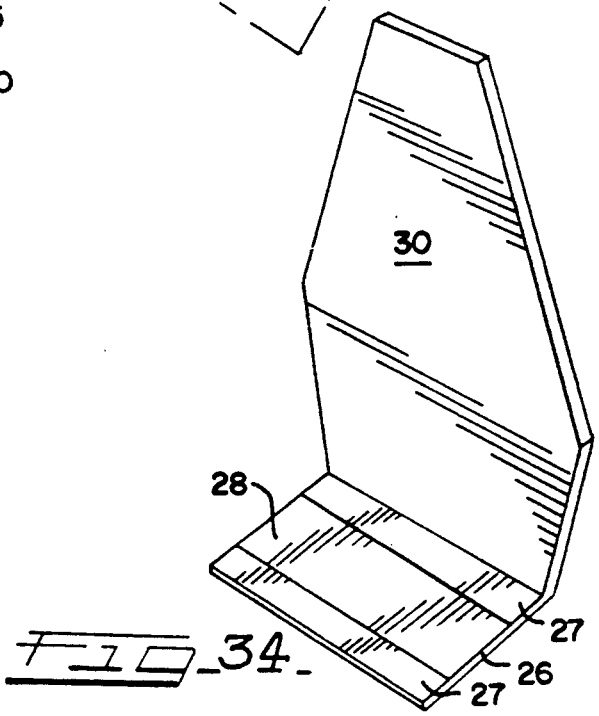

APPARATUS FOR HOLDING DENTAL FLOSS CONTAINERS AND SPOOLS

The present invention is a continuation-in-part of co-pending parent application Ser. No. 07/225,775, filed Jul. 29, 1988.

This invention relates specifically to the supporting and dispensing of dental floss either in spools or from variously sized and shaped containers available in the marketplace.

It is a well known fact that daily and consistent use of dental floss for removing bacterial plaque in proximity to the gums and between the teeth is recommended by dental authorities in the furtherance of good oral hygiene practice. One of the ways in order to induce the use of dental floss is by making the floss handy and convenient to use at various locations. The fact that most dental floss containers are hidden away in a medicine cabinet or bathroom drawer prevents the user from using dental floss daily.

The present invention solves the need for a suitable reminder to stimulate the user to utilize dental floss.

BACKGROUND OF INVENTION

Various type of dental floss dispensing devices have been known in the past including devices having various features which are attractive to children and adults. U.S. Pat. No. 4,308,880 to Graves discloses an animated dental floss dispenser which simulates the flossing of a person's teeth with the simultaneous dispensing of a dental floss. U.S. Pat. Nos. Des. 176,090, 154,894 and 76,490 disclose various ornamental designs for dental floss holders.

U.S. Pat. No. 2,967,651 to Zackheim, et al., discloses a font for dispensing dental floss, but teaches nothing in regard to holding variously sized dental floss containers.

U.S. Pat. No. 2,929,541 to Castelli, et al., discloses a dispenser for dental floss and other filaments which requires a specific spool-type shape to be held for dispensing thereof and which is limited only to that shaped spool.

U.S. Pat. No. 3,787,859 to Chambers discloses a dental floss holder which holds a spool of floss in a taut position between a pair of spaced prongs for dispensing. Although this device holds two different types of dental floss spools, it is not a universal type of device for containing various size containers.

U.S. Pat. No. 1,455,673 to Shalek discloses a wall mounted dental floss dispenser which holds only a single specific shaped dental floss spool. The present invention is adaptable to receive and dispense floss from all types and shapes of floss containers.

The above references all have various shortcomings which the present invention obviates. Many of the above floss holders are unable to receive and dispense dental floss housed in various commercially available shaped containers or floss on spools without containers. The present invention, as shown in the following embodiments, allows numerous shaped containers and spools to be housed and then readily dispensed for us.

SUMMARY OF INVENTION

A wall mountable apparatus for holding dental floss containers and spools having in the preferred embodiment a series of simultaneous contours and cutouts in order to receive and retain variously shaped dental floss containers and spools. Other embodiments include a clamp-like bracket for grasping the floss container, an axial spool or bobbin support, a universal cavity for supporting non-uniform and uniform dental floss containers and spools, a hook-and-fastener type support conventionally referred to as "Velcro", magnetic or other adhesive supports, such as a wax conventionally referred to as "Tacky Wax", and various strap or rubberband adhesives. Each of the embodiments disclosed will readily dispense the floss contained and because of their vertical surface or counter top mountability, serve as a reminder to floss daily due to the constant visibility of the present invention.

It is the principal object of the present invention to provide a dental floss holder which will accommodate all sizes and shaped containers of dental floss as well as those without containers which are contained on spools.

It is a further object of the present invention to provide a dental floss holder which will receive commercially available containers of floss without having to remove the floss contained for mounting into the invention.

It is a further object of the present invention to dispense dental floss with a simple mechanism having few working parts.

It is another object of the present invention that the apparatus hold the floss in a hygienic and sanitary manner.

It is yet another object of the present invention that the apparatus safely afford the portioned dispensing of floss to small children.

It is yet another object of the invention to provide a suitable housing and dispenser for dental floss that is aesthetically pleasing and corresponds with any of the surrounding decor.

Numerous other advantages and features of the invention will become readily apparent from the following detailed description of the preferred embodiment of the invention, from the claims, and from the accompanying drawings, in which like numerals are employed to designate like parts throughout the same.

BRIEF DESCRIPTION OF THE DRAWINGS

A fuller understanding of the foregoing will be had by reference to the accompanying drawings wherein:

FIG. 1 is a perspective view of the preferred embodiment of the apparatus for holding dental floss mounted on a vertical surface;

FIG. 2 is an internal perspective view of the preferred embodiment of FIG. 1;

FIG. 9 is a rear cross-sectional view of the preferred embodiment receiving variously shaped floss containers;

FIG. 10 is a rear cross-sectional view of the preferred embodiment supporting various shaped floss containers;

FIG. 11 is a rear cross/sectional view of the preferred embodiment for receiving a cylindrical spool;

FIG. 12 is a perspective view of a clamp-type embodiment of the present invention;

FIG. 13 is a perspective view of a universal cavity-type embodiment of the present invention; and FIG. 14 is a side view of the fastening hinge for the universal cavity-type embodiment of the present invention;

FIG. 15 is a front perspective exploded view of "Velcro" type fastener embodiment of the invention for adhering a dental floss container within the holder of the present invention;

FIG. 16 is a cutaway rear elevational view of the "Velcro" type fastener shown in FIG. 15;

FIG. 17 is a cross-sectional side view of the "Velcro" type fastener embodiment of the present invention shown in FIG. 15;

FIG. 18 is a cross-sectional front view of an alternate embodiment of the present invention showing an unrestrictive cavity means for holding a dental floss container within the invention;

FIG. 19 is a cutaway lower rear elevational view of another embodiment of the present invention, showing a dental floss container with an adhesive magnet to magnet with adhesive backing for mounting to the rear wall of the present invention;

FIG. 20 is a partial cross-sectional side view of the lower end of the present invention as embodied in FIG. 19, showing an adhesive such as a magnet adhered to the dental floss container and to the rear wall of the invention to affix the container thereto;

FIG. 21 is an exploded cross-sectional side view of an alternate embodiment of the present invention showing a lock-fit mechanism for adhering a dental floss container to the rear wall of the invention;

FIG. 22 is a cross-sectional side view of the embodiment of the present invention shown in FIG. 21, depicting the lock-fit adherence of the container to the rear wall of the invention;

FIG. 23 is a cutaway front view of the unrestrictive cavity embodiment of the invention shown in FIG. 18, depicting the dental floss container drawn to the top of the invention when floss is pulled for use from the invention;

FIG. 24 is a front cross-sectional view of an alternate embodiment of the present invention showing an adhesive, such as that conventionally referred to as "Tacky Wax", applied between the dental floss container and the rear wall of the invention for affixing the container thereto;

FIG. 25 is a front perspective cutaway view of the invention shown in FIG. 24;

FIG. 26 is a front perspective exploded view of an alternate embodiment of the present invention showing a holder for a dental floss container designed to be recessed within a support member such as a wall or cabinet such that the outer face is flush with the support member exterior surface;

FIG. 27 is a cutaway front elevational view of an alternate embodiment of the present invention showing an adjustable length strap fastener adhered to the rear wall of the invention for wrapping around and holding in place a dental floss container therewithin;

FIG. 28 is a cutaway front elevational view of the invention shown in FIG. 27 using a hook and fastener type strap attachment, such as that conventionally referred to as "Velcro", for releasably fastening a dental floss container in place within the invention;

FIG. 29 is a cutaway front elevational view of the invention shown in FIGS. 27 and 28, depicting the fastener strap wrapped around and retaining a dental floss container within the invention;

FIG. 30 is a front view of a packet of floss;

FIG. 31 is a front view of a packet of floss with the floss exposed;

FIG. 32 is a partial cutaway perspective view of an alternative embodiment of the invention dispensing floss packets;

FIG. 33 is a side cross-sectional view of a spring loaded alternate embodiment of the invention dispensing floss packets; and FIG. 34 is a partial internal perspective view of an alternative embodiment of the invention dispensing floss packets.

DESCRIPTION OF PREFERRED EMBODIMENT

Figure 4:
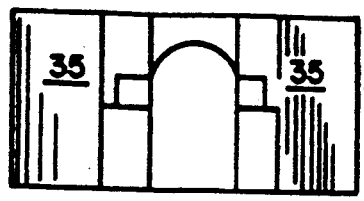
FIG. 4 is a top plan rear view of the contoured internal retainer of the preferred embodiment of FIG. 1.
Figure 3:
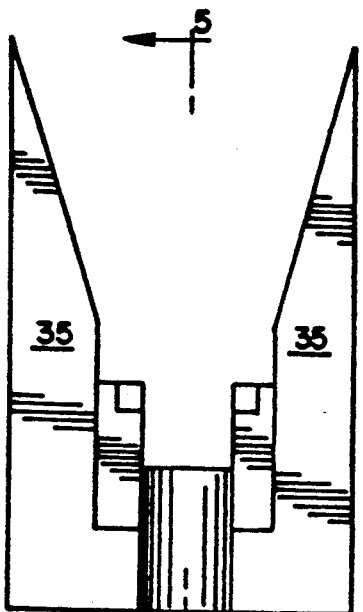
FIG. 3 is a rear elevational view of the contoured internal retainer of the preferred embodiment of FIG. 1.

While this invention is susceptible of embodiment in many different forms, there is shown in the drawings and will herein be described in detail a number of embodiments of the invention. The invention disclosed herein is equally applicable to many other shaped and housed dental floss containers besides the embodiments shown and described herein. It should be understood that the present disclosure is to be considered an exemplification of the principle of the invention and is not intended to limit the spirit and scope of the invention and/or claims to the embodiments illustrated.

Referring now to the figure drawings, FIG. 1 is a perspective view of one of the preferred embodiments of the apparatus 10 for holding dental floss 5 mounted on a vertical surface 15. Vertical surface 15 in a practical home application, may be a bathroom wall. Likewise, other vertical surface applications such as oral hygienist, dentist or other dental professionals offices' are also appropriate. A dispensing opening 7 and cutting means 20 are positioned on the uppermost portion of the apparatuses' front housing 25. Said front housing 25 is hinged or fingered and slotted 110 at the base to allow internal access to the apparatus 10. Rear wall 30 is shown only in partial view.

Shown in FIG. 2 is a contoured internal cavity 35 formed of a resilient material within apparatus 10. The resilient material may be of conventional material such as open or closed cell foam or neoprene, known for its shape retension and its gripping ability to receive and support currently available variously shaped dental floss containers 40. The cavity 35 depicted in phantom lines of FIGS. 9 and 10 allows various dental floss containers 40 to be received and retained by the resilient material.

FIG. 11 depicts a cylindrical spool embodiment with a threaded shaft 50 axially positioned and supporting a spool of dental floss 45 and retained by a thumb screw 55.

FIG. 12 depicts the apparatus 10 of the present invention as a clamp-type holder of dental floss containers which receive and retain the container 40 as shown.

FIG. 13 depicts the apparatus 10 having a universal chamber with spring biased retaining means.

Guide 12 is further shown in FIGS. 9-11.

Figure 5:
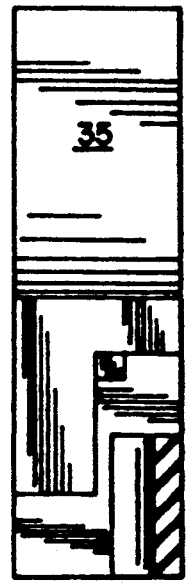
FIG. 5 is a side elevational view along line 5—5 of FIG. 3.
Figure 6:
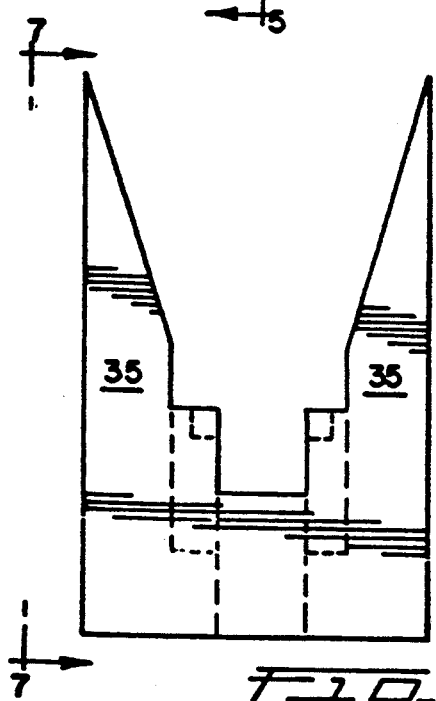
FIG. 6 is a front elevational view of the contoured internal retainer of the preferred embodiment of FIG. 1.
Figure 7:
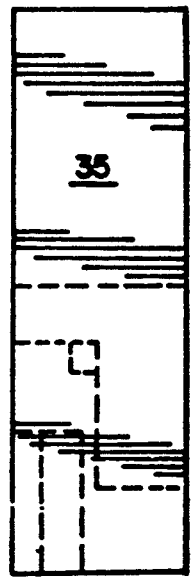
FIG. 7 is a side elevational view along line 7—7 of FIG. 6.
Figure 8:
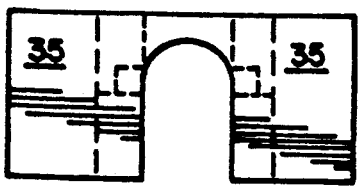
FIG. 8 is a bottom plan view of the preferred embodiment of FIG. 1.

Shown in FIGS. 4-8 are various views of the contoured cut-outs of the cavity 35 for apparatus 10. The conception of the various contours in the preferred embodiment is based on the various shapes and sizes of containers for dental floss currently available. Although the preferred embodiment relates to currently available shaped containers, in the future, other shaped containers should readily be accommodated by the present invention. The cavity 35 as stated above is configured to resiliently grip a container 40 so that as floss 5 is dispensed from the apparatus 10, the container 40 does not move, thereby preventing fouling of the floss 5 within the apparatus 10 and also prevents breakage and the resulting hassle of rethreading the floss 5. Furthermore, the apparatus 10 ensures the ease of dispensing dental floss 5 without tangling or being exposed to unsanitary conditions. The contours shown in FIGS. 4-8 are intended to functionally receive variously shaped containers 40 without conflict with the other contours for other shaped and sized containers 40.

In FIG. 9, generally rectangular shaped containers 40 (each shown in phantom) are received and positioned within cavity 35 of apparatus 10. Similarly, in FIG. 10 hexagonally shaped, rectangular and cube shaped containers 40 (each shown in phantom) are likewise shown received and positioned within cavity 35 of apparatus 10.

FIG. 11 is a rear cross-sectional view of one of the preferred embodiments supporting a spool 45 of dental floss 5. The spool 45 is supported and retained by a fastening means which may consist of a threaded shaft 50 which is coaxially positioned within said spool 45 and retained by retainer or wing nut 55. Shaft 50 is threaded along its entire length so as to accommodate spools 45 of various lengths.

FIG. 12 is a partial perspective view of an alternative embodiment of the present invention configured as a clamp-type holder 60. A guide rail 65 is positioned usually in a horizontal direction with adjustable steps 70 formed therein to hold and retain gripping arms 75. Gripping arms 75 with gripping means 77 complement each other in gripping and supporting variously shaped containers 40. A rectangular container 40 is only partially shown. A resilient material is shown contained within gripping arms 75. It is intended, though not required, that clamp-type holder 60 be positioned within and between front housing 25 and rear wall 30 for mounting on a vertical surface 15.

FIGS. 13 and 14 depict alternative embodiments of the present invention. In FIG. 13, a universal cavity-type embodiment is shown. A conventional dental floss container 40 is retained and supported (shown in a floating state) by a resilient material which is partially housed in a wall mountable backing 80. Backing 80 may be configured with locking screw guides 85 on each side (only two shown) or by some other conventional vertical surface or wall fastening method. A front retaining housing 90 is shown with a resiliently biased retaining means 95 which is biased by springs 100 or other conventional biasing means. Rear wall retaining means 120 is affixed to backing 80 and holds and supports container 40. Finger and hold catches 105 are used to removably retain housing 90 to backing 80. Bottom hinging arms and holes 110 likewise removeably retain housing 90 to backing 80. FIG. 14 is a cross-sectional view of bottom hinging arms and holes 110.

In FIGS. 15 through 17, generally shown is an alternate embodiment of the invention depicting the apparatus 10 as a hook and loop type fastener, [conventionally referred to as "Velcro",] having holder backing 120 and floss backing 125, whereby holder backing 120 is affixed to the rear wall 30 of the apparatus 10, and floss backing 125 is affixed to the container 40 to releasably grip the holder backing 120 when contacted with the floss backing 125 for retaining the container 40 within the apparatus 10.

FIGS. 18 and 23 depict an alternate embodiment of the invention in which the container 40 is loosely retained within the cavity 35 without being affixed to the rear wall 30. FIG. 18 shows the container 40 resting on the bottom of the apparatus 10. When the floss 5 is pulled out of the opening 7 for use, the container 40 bobs up to the opening 7 to provide tension against the apparatus 10 by the container 40, as shown in FIG. 23. The floss 5 is then removed and severed by the cutter 20. The container 40 subsequently returns to the bottom of the apparatus 10 until used next.

FIGS. 19 and 20 depict an alternate embodiment of the present invention in which wall magnet 130 and floss magnet 135 removably affixes the container 40 to the rear wall 30 of the apparatus 10 for retention within the cavity 35. In this embodiment, wall magnet 130 is fixedly secured to the rear wall 30 by adhesive 131 and floss magnet 135, having reverse polarity of wall magnet 130, is fixedly secured to the container 40 by adhesive 136. Magnets 130 and 135 are cooperatively associate fasteners to removably adhere the container 40 to the rear wall 30 when floss magnet 135 is paired with wall magnet 130.

In FIGS. 21 and 22, an alternate embodiment of the invention is shown as a releasably interlocking fit of wall member 140 and container member 145. In this embodiment, wall member 140 has an opening 141, and is fixedly secured to rear wall 30. Wall member 140 is configured to cooperatively associate with container member 145, which has a flange member 146 and is fixedly secured to the container 40. When flange member 146 is inserted into opening 141, container member 145 releasably interlocks with wall member 140 to adhere the container 40 to the rear wall 30.

FIGS. 24 and 25 depict another preferred embodiment of the present invention. In this embodiment, an adhesive 150 such as that conventionally referred to as "Tacky Wax" is applied to the rear wall 30, against which the container 40 is pressed to removably adhere the container 40 to the rear wall 30 within the cavity 35 of the apparatus 10.

FIG. 26 shows yet another preferred embodiment of the invention. In this embodiment, the apparatus 10 is recessed within a support member 15 such as a wall or cabinet such that the front wall 25 is flush with the exterior surface of the support member 15.

FIGS. 27 through 29 depict another preferred embodiment of the present invention which utilizes a strap 150 secured to the rear wall 30, said strap 150 having strap ends 151 and 152, which are fastened by clip means 153(a) (b), as shown in FIG. 27, or hook and loop type fastener means 154(a) (b) as shown in FIG. 28, for wrapping around the container 40 to hold it in place within the apparatus 10, as shown in FIG. 29. In FIG. 27, strap ends 151 and 152 clip together using clip means 153a and 153b to releasably retain a container 40, around which strap ends 151 and 152 wrap, within the apparatus 10. In FIG. 28, strap ends 151 and 152 fasten together by adhering the hook and loop type fasteners, conventionally referred to as "Velcro", represented by units 154a and with that of 154b to releasably retain the container 40 around which strap ends 151 and 152 wrap, in place within the apparatus 10.

The operation of the above described embodiments is simply and effectively described as follows. A conventionally shaped floss container 40 is positioned into cavity 35 such as shown in FIGS. 9, 10, 15, 18, 26 and 27, and retained in cavity 35. Alternatively, a spool of floss 45 is axially mounted on shaft 50 and retained by nut 55. Floss 5 is threaded through guide 12, opening 7 and cutter 20. Front housing 25 is closed by complementary fitting against rear wall 30. The user grasps the floss 5 by hand from apparatus 10 through opening 7 and out of container 10 and detaches the desired amount for use by cutter 20.

The clamp-type embodiment as shown in FIG. 12, retains and supports a variously sized container 40 between gripping arms 75 by manually adjusting arms along guide rail 65 by adjustable steps 70. The floss 5 is dispensed in the same fashion as described above.

Shown in FIGS. 30-34 are depicted alternative embodiments of the present invention in which floss 5 is axially wrapped around a card 4 as shown in FIG. 31 and inserted into a packet or envelope container 6 (FIG. 30) in order to keep the floss 5 clean and neatly dispensable.

Floss 5 in the packets 6 may be dispensed through bottom of apparatus 10 as seen in FIG. 32. Stacked by gravity in FIG. 32 the lower panel is shown in FIG. 34 as the user pulls the packet 6 through the open area 28 of housing floor 26, the available packet 6 is touched and can be pulled forward through area 29 as seen in FIG. 32.

In FIG. 33, the spring and plunger device 100 is depicted pushing the stack of packets 8 which forces the bottom packet 6 forward and down to the lower panel 26 and out of the apparatus 10 at the opening 29.

Once the packet 6 is dispensed through 29, the floss 5 can be removed and unwound from card 4 for use. As shown in FIG. 33 the apparatus 10 can be wall or vertically mounted.

The effective dental floss holder of the present invention encourages dental floss use in accordance with good dental hygiene practices by being a familiar and convenient bathroom accessory.

The foregoing has presented only a few of the various embodiments of the present invention and it is understood that these embodiments have been presented by way of example only. For example, a timing device or alarm device to serve as a reminder to floss daily. It is expected that others will perceive differences which, while bearing from the foregoing, do not depart from the spirit and scope of the invention herein described and claimed.

What we claim:

1. A dental floss container holder and floss dispenser, comprising:
   a polygonal shaped housing, said housing having an interior and an exterior;
   means for access within said polygonal shaped housing;
   retaining means configured to accommodate variously shaped and sized dental floss containers, said retaining means positioned within housing, said retaining means comprised of a hook and loop fastener, said fastener comprised of a housing member fixedly secured to said interior of said housing and adapted to cooperatively associate with a container member which is fixedly secured to said dental floss container, whereby said members releasable engage for retaining said container within the interior upon being pressed together;
   guide means for directing floss from the container retained within said retaining means from the interior of said housing to the exterior of said housing; and
   cutting means for detaching the floss from the dental floss container holder and floss dispenser, said cutting means positioned on the exterior of said housing.

2. A dental floss container holder and floss dispenser, comprising:
   a polygonal shaped housing, said housing having an interior and an exterior;
   means for access within said polygonal shaped housing;
   retaining means configured to accommodate variously shaped and sized dental floss containers, said retaining means positioned within housing, wherein said retaining means is tacky and placed between said housing and said container for releasably affixing said dental floss container to said interior of said housing;
   guide means for directing floss from the container retained within said retaining means from the interior of said housing to the exterior of said housing; and
   cutting means for detaching the floss from the dental floss container holder and floss dispenser, said cutting means positioned on the exterior of said housing.

3. A dental floss container holder and floss dispenser, comprising:
   a polygonal shaped housing, said housing having an interior and an exterior;
   means for access within said polygonal shaped housing;
   retaining means configured to accommodate variously shaped and sized dental floss containers, said retaining means positioned within housing, wherein said retaining means is comprised of a lock fit unit, having a female member fixedly secured to said interior of the housing, said female member having a recess, and a male member fixedly secured to said dental floss container, said male member having a flange portion adapted to cooperatively associate in releasable interlocking fit with said female member upon insertion of said flange within said recess;
   guide means for directing floss from the container retained within said retaining means from the interior of said housing to the exterior of said housing; and
   cutting means for detaching the floss from the dental floss container holder and floss dispenser, said cutting means positioned on the exterior of said housing.

4. A dental floss container holder and floss dispenser, comprising:
   a polygonal shaped housing, said housing having an interior and an exterior;
   means for access within said polygonal shaped housing;
   retaining means configured to accommodate variously shaped and sized dental floss containers, said retaining means positioned within housing, wherein said retaining means is comprised of a fastener strap having two end portions and a midsection, said midsection being affixed to said interior of said housing, said end portions having closure means whereby said fastener strap is wrapped around a dental floss container placed within said interior over said midsection, said end positions being releasably connected by operation of said closure means to retain said container within said interior of said inventions;

guide means for directing floss from the container retained within said retaining means from the interior of said housing to the exterior of said housing; and cutting means for detaching the floss from the dental floss container holder and floss dispenser, said cutting means positioned on the exterior of said housing.

5. A dental floss container holder and floss dispenser, comprising:

a polygonal shaped housing, said housing having an interior and an exterior;

means for access within said polygonal shaped housing;

retaining means configured to accommodate variously shaped and sized dental floss containers, said retaining means positioned within housing, wherein said retaining means is comprised of a set of magnets having a first magnet being fixedly secured to said container, and a second magnet having reverse polarity relative to said first magnet and being fixedly secured to said interior of said housing, whereby said container is releasably adhered to said interior by placing said first magnet in cooperative magnet association with said second magnet;

guide means for directing floss from the container retained within said retaining means from the interior of said housing to the exterior of said housing; and cutting means for detaching the floss from the dental floss container holder and floss dispenser, said cutting means positioned on the exterior of said housing.

6. A dental floss container holder and floss dispenser, comprising:

a polygonal shaped housing, said housing having an interior and an exterior; means for access within said polygonal shaped housing;

retaining means configured to accommodate variously shaped and sized dental floss containers, said retaining means positioned within housing;

guide means for directing floss from the container retained within said retaining means from the interior of said housing to the exterior of said housing;

cutting means for detaching the floss from the dental floss container holder and floss dispenser, said cutting means positioned on the exterior of said housing; and support means for receiving said housing, said support means consisting essentially of a rigid vertical planar member having a cavity of like polygonal shape and size to said housing, whereby said housing is inserted into said cavity for support of said dispenser within said rigid vertical planar member.

7. The invention recited in claim 6, wherein said rigid vertical planar member is a wall.

8. The invention recited in claim 6, wherein said rigid vertical planar member is an article of furniture.

9. A dental floss container holder and floss dispenser, comprising:

a polygonal shaped housing, said housing having an interior and an exterior, and within said housing a dental floss container is housed;

means for accessing dental floss stored within said polygonal shaped housing;

guide means for directing floss from the container stored within said interior of said housing to said exterior of said housing; and cutting means for detaching the floss from the dental floss container holder and floss dispenser, said cutting means positioned on the exterior of said housing; said container resting freely within said housing and bobbing up to bear against said guide means from within said interior of said housing when floss is pulled out of said dispenser, said container then dropping down to resume a resting position within said housing after the floss is detached using said cutting means.

10. The invention of claim 6, wherein said retaining means is configured to retain an elongated axial spool of dental floss.

11. The invention of claim 10, wherein said retaining means is a resilient strap.

12. A dental floss container holder and single-use floss packet dispenser, comprising:

a housing, said housing having a front and back portion, said front and back portions each having an interior and exterior;

retaining plunger means affixed to the interior of said portion of said housing, said plunger means is biased away from said housing such that when said front and back portions of said housing are complementary fastened together, said plunger means forces the container against the single-use floss packets;

releasable fastening means for fastening said front and back portions of said housing together.

13. The invention of claim 12, wherein said housing is wall mountable.

14. The invention of claim 1, 2, 3, 4, 5, or 11, wherein said housing is wall mountable.

* * * * *